United States Patent [19]

Shapiro

[11] Patent Number: 4,819,635

[45] Date of Patent: Apr. 11, 1989

[54] TUBULAR MICROSURGERY CUTTING APPARATUS

[76] Inventor: Henry Shapiro, 328 Downham Ct., Walnut Creek, Calif. 94598

[21] Appl. No.: 98,330

[22] Filed: Sep. 18, 1987

[51] Int. Cl.[4] .............................................. A61B 17/20
[52] U.S. Cl. ....................................... 128/305; 604/22; 128/752
[58] Field of Search ............... 128/305, 752, 753, 754, 128/755; 604/22, 35, 264, 267, 275

[56] References Cited

U.S. PATENT DOCUMENTS

| | | | |
|---|---|---|---|
| 3,815,604 | 6/1974 | O'Malley et al. | 128/305 X |
| 4,203,444 | 5/1980 | Bonnell et al. | 128/305 X |
| 4,210,146 | 7/1980 | Banko | 128/305 |
| 4,662,869 | 5/1987 | Wright | 604/22 |
| 4,678,459 | 7/1987 | Onik et al. | 128/305 X |
| 4,696,298 | 9/1987 | Higgins et al. | 123/305 |
| 4,735,605 | 4/1988 | Swartz | 128/305 X |

Primary Examiner—Willis R. Wolfe
Attorney, Agent, or Firm—George W. Wasson

[57] ABSTRACT

A tubular microsurgery cutting apparatus is disclosed having an outer tubular member and an inner tubular sleeve reciprocatable within the outer tubular member. The inner tubular sleeve is formed near its cutting end with an enlarged diameter, plated and lapped area having a spiral axial slot extending away from the cutting end along the sleeve. This construction provides for a smooth, friction reducing engagement between the sleeve and the inside of the outer tubular member at the cutting end and a substantially non-frictional relationship of the inner sleeve and outer member throughout the remainder of the apparatus.

8 Claims, 2 Drawing Sheets

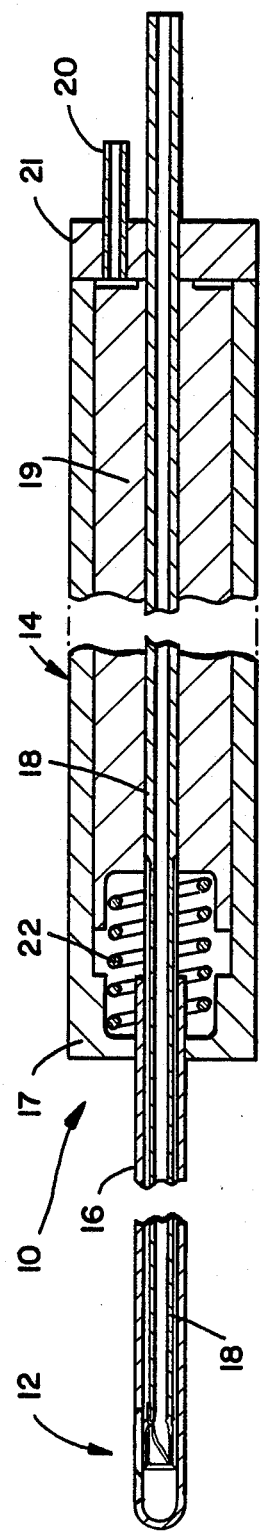
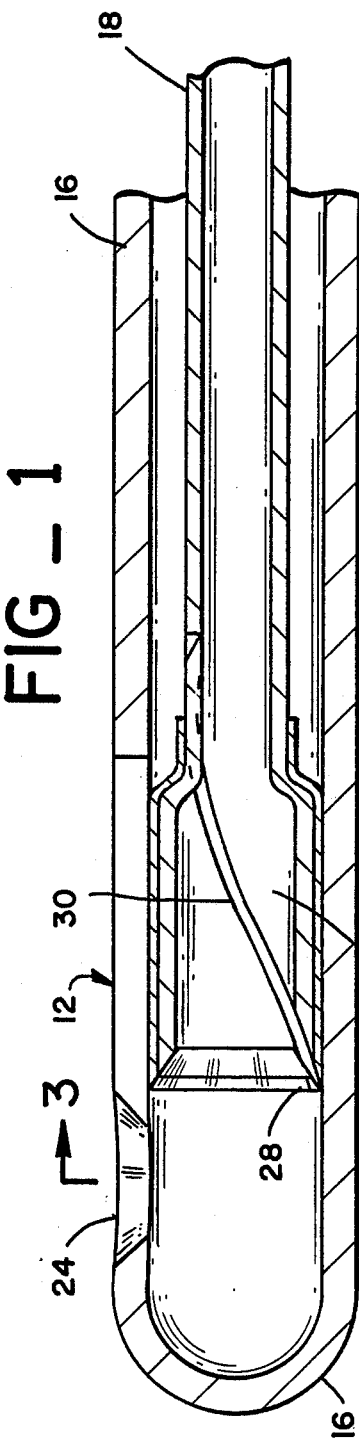
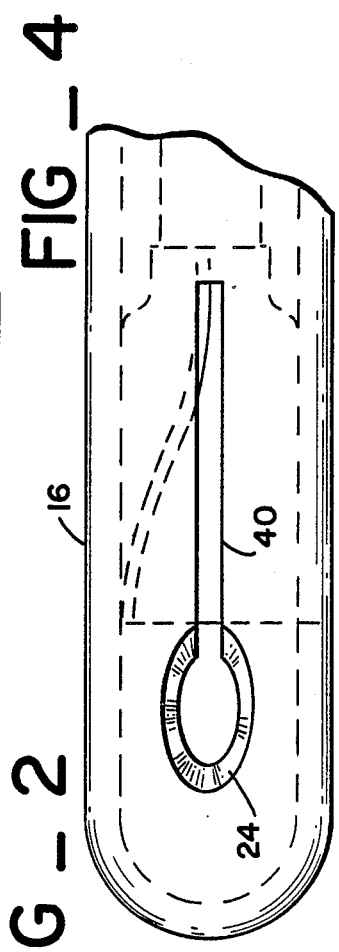
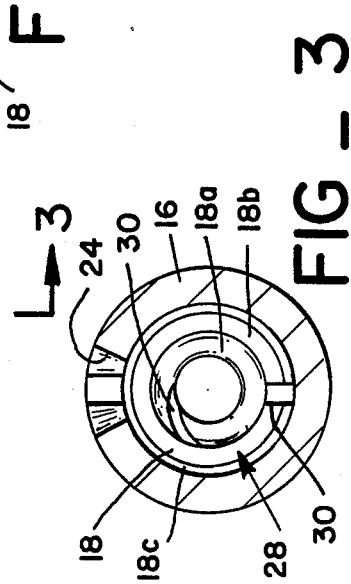

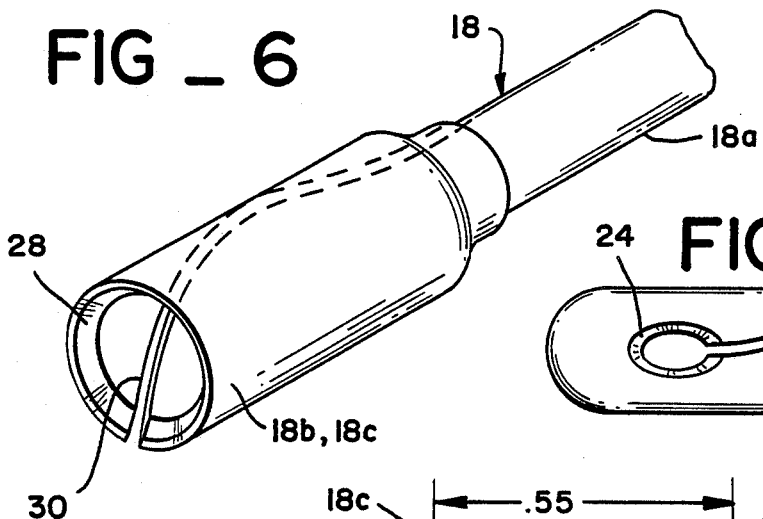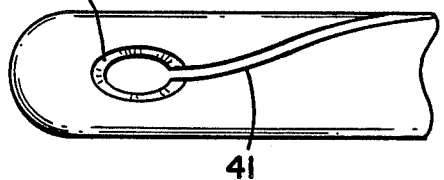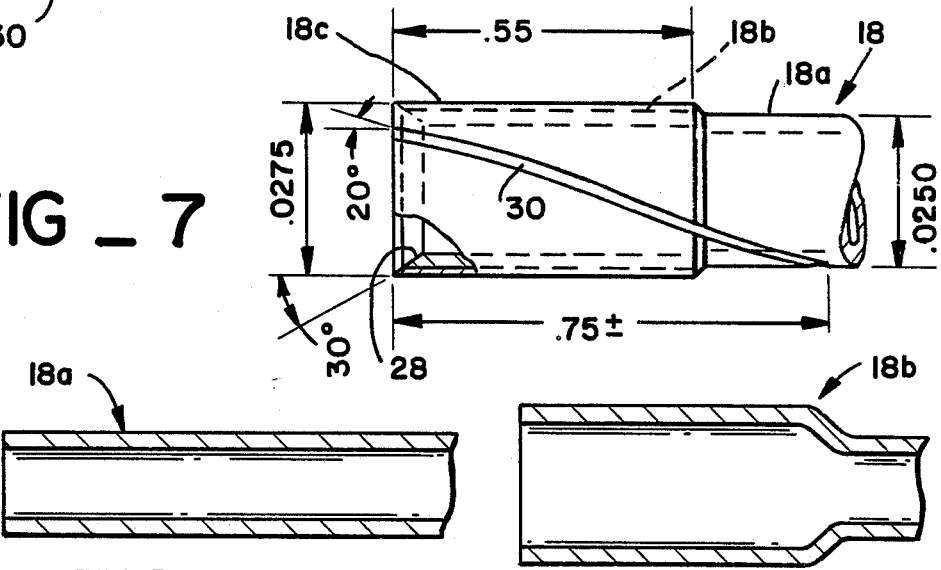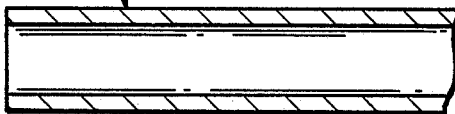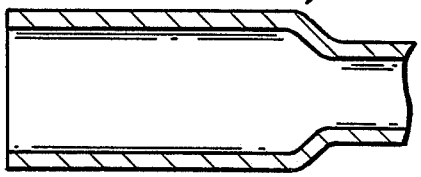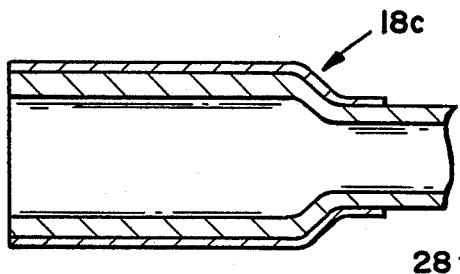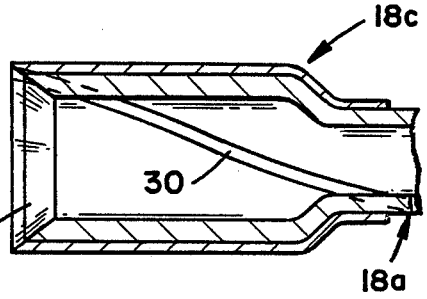

TUBULAR MICROSURGERY CUTTING APPARATUS

FIELD OF THE INVENTION

This invention relates generally to surgical cutting instruments and more particularly to an apparatus for use in effecting intricate surgery using an elongated tubular instrument that is inserted into the region where the surgery is to be performed. One particular use of the apparatus is in performing opthalmic surgery.

BACKGROUND OF THE INVENTION

The use of a pair of elongated tubes which reciprocate relative to each other to perform cutting operation in vitreous surgery is known. O'Malley and Heintz, U.S. Pat. No. 3,815,604 dated June 11, 1974, shows a cutting instrument for use in vitreous surgery in which the inner tube reciprocates in the direction of the longitudinal axis of the tubes. As the end of the inner tube reciprocates across a window in the elongated tube, the shearing action is performed. O'Malley teaches that the cutting action of the instrument is enhanced by the use of a flared inner member to maintain a snug fit between the two tubular members. Others including Seiler, U.S. Pat. No. 4,011,869 dated Mar. 15, 1977, have addressed the problem of close machining tolerances and the friction that is created between the two tubular members of the O'Malley instrument in the reciprocating operation of the inner tube.

A surgical cutting instrument of the type disclosed by O'Malley and others should be easily handled by the person performing the surgery, should be strong in compression along its elongated axis, should be capable of avoiding non-elastic bending along its longitudinal axis, should be efficient in the reciprocational action of its inner parts, and effective in performing the desired internal surgery. The instrument of the present invention is directed to all of these needs.

A trend in surgical practices has been toward the use of instruments that will be disposable after a single use. Such a trend has increased the expenses in performing surgery that uses such instruments because of the one time use of the instruments. An instrument used one time should be constructed with the same care and precision as an instrument that will have several uses so the user frequently pays as much for the single use instrument as the multiple use instrument. When the instrument is destroyed after a single use, the equipment portion of the expense of the surgery must have been increased. In some cases the cost of a disposable instrument is kept within reason by reducing the material costs and the construction costs. Where instruments are to have more than a single use there is a reason to construct the instrument with more attention to the life of the materials used in the construction and a reason to give more attention to the wear induced frictions within the instrument. The surgical instrument of the present invention is designed with particular attention to the possibilities of more than a single use and with attention to the materials that will reduce friction and maintain cutting efficiency through several uses of the instrument.

It is an object of the present invention to provide a tubular microsurgery cutting apparatus that includes an inner and an outer tubular member with the inner member constructed in a form that reduces the friction between the inner and outer tubular members as the inner tube is reciprocated within the outer tube.

A further object of the present invention in accord with the preceding object is to provide an inner tubular sleeve that maintains efficient cutting engagement between the inner sleeve and outer tubular member while reducing the friction between the inner sleeve and outer tubular member during reciprocation of the inner sleeve within the outer tube.

A further object in accord with the preceding objects is an inner tubular sleeve provided with an expanded diameter at its cutting edge and with a construction that maintains the expanded diameter portion in working contact with the inside surface of the outer tubular member.

A further object in accord with the preceding objects is a tubular microsurgery cutting apparatus including an inner tubular sleeve with a spiral slot construction axially along the sleeve.

Further objects and features of the present invention will be readily apparent to those skilled in the art from the appended drawings and specification illustrating preferred embodiments wherein:

BRIEF DESCRIPTION OF THE DRAWINGS

FIG. 1 is a cross-sectional assembly view of the tubular microsurgery cutting apparatus of the present invention.

FIG. 2 is an enlarged sectional view of the cutting end of the apparatus of FIG. 1.

FIG. 3 is a sectional view taken along the lines 3—3 of FIG. 2.

FIG. 4 is a top plan view of the outer tubular member.

FIG. 5 is a top plan view of an alternative form of the outer tubular member.

FIG. 6 is a perspective view of the inner tubular sleeve of the apparatus of FIG. 1.

FIG. 7 is an enlarged side elevational view of the cutting end of the inner tubular sleeve in accord with the present invention.

FIGS. 8, 9, 10 and 11 are progressive drawings illustrating the formation of the inner tubular sleeve from tubular stock to finished form.

DESCRIPTION OF THE PREFERRED EMBODIMENT

Referring to FIG. 1 of the drawings in detail, reference numeral 10, designates the assembled tubular microsurgery cutting apparatus of the present invention with its elongated tubular cutting end 12 and its stationary or hand held end 14, hereinafter referred to as the driving end. Within the stationary driving end 14 the reciprocating motion is developed for a member in the cutting end 12 of the apparatus. In the FIG. 1 illustration the apparatus 10 is shown in section and both the cutting end 12 and the driving end 14 have their longitudinal dimension interrupted to permit illustration of the assembly. It should be understood that the cutting end 12 may be as long as 30 centimeters and the driving end 14 is proportionally long enough for the user to have a comfortable hand grip on that portion of the apparatus. The overall apparatus should be easily manipulated in surgical usage. The cross-sectional dimension of the cutting end 12 of the apparatus is shown enlarged for illustration purposes; the outside diameter of the outer tubular member 16 may be in the range of from 0.05 to 0.1 centimeter.

As shown in FIG. 1 the apparatus includes an outer tubular member 16 having an open end and a closed end with the open end fixed to the housing 17 of the driving end 14 and an inner tubular sleeve 18 having an open end and a cutting end that is adapted to reciprocate within the outer tubular member 16. Those who are familiar with instruments of the type described in this specification frequently refer to the instrument as a probe, the outer tubular member as the needle portion of the instrument, and to the inner tubular sleeve 18 as the cutter portion of the instrument. Those and other terms for the elements of the apparatus are intended to be included in the terms "outer tubular member" and "inner tubular sleeve" as used in this specification. The open end of the inner tubular sleeve 18 is fixed to a reciprocatable piston 19 within the housing 17 of the driving end 14 and the cutting end is positioned within the outer tubular member 16 near the cutting end 12 of the apparatus. The housing 17 as shown in the present apparatus is cylindrical and substantially air tight and its end cap 21 is adapted to enclose a cylindrical piston 19 for reciprocating movement. A source of pulsing air pressure or other driving force is supplied through end cap 21 at tube 20 to force the piston toward the cutting end 12 of the apparatus against a spring 22 that biases the piston toward the end cap 21. With the inner tubular sleeve 18 fixed to the piston 19 the inner tubular sleeve 18 is caused to reciprocate within the outer tube 16. The inner tube 18 is also shown as a continuous tube extending beyond the end of the driving end 14 of the apparatus and, in a preferred form, the inner tubular sleeve 18 is connected to an external vacuum source, not shown, that draws material through the inner tubular sleeve 18 from the cutting end 12 toward the driving end 14. The type of the material drawn through the inner tubular sleeve 18 should be well known to those familiar with microsurgery apparatus.

FIG. 2 is an enlarged cross-sectional view of the tip of the cutting end 12 showing the outer tubular member 16 and the inner tubular sleeve 18. The outer tubular member 16 has a cutout opening defining an entry port 24 having a particular form that will be further described hereinafter. The inner tubular sleeve 18 has a cutting tip at 28 at the open end of the member and is formed with a spiral slot at 30 extending from the tip 28 toward the driving end 14 of the apparatus 10. The form of the cutting end of the inner tubular sleeve 18 is exagerated in FIG. 1; its formation will be further described hereinafter. The form of the cutting tip 28 and the body of the inner tubular sleeve at the cutting end is intended to provide a firm and smooth working contact between the outer surface of the inner tubular sleeve 18 and the inner surface of the outer tubular member 16, at least at the entry port 24. That form provides for reduction in the friction contact between the inner sleeve and the outer tubular member at the cuting end while preferably, substantially eliminating contact between the inner and the outer member except at the cutting end. For example, the clearance along the interior of the tubular member may be 0.001 at each side along the major portion of the member whereas there should be slidable, working contact between the enlarged cutting end and the inner surface of the tubular member.

Referring now to FIGS. 3, 7 and 8-11 for details in the form and construction of the inner tubular sleeve 18, it is intended to form the inner tubular sleeve from tubular stock 18a as shown in FIG. 8. The specification for a material for the inner tubular stock is based upon the service to be performed. The material must be adapted to work within a surgical environment, it should be strong enough in compression to avoid damage as it is reciprocated within the outer tubular member, and it must be of a material that will permit it to be further formed as will be described.

As shown in FIG. 4 the end of the tubular stock 18a is formed at 18b to increase its inner and outer diameter axially along the stock while retaining it tubular form. The length of the increased diameter 18b will be described hereinafter; however, it should be understood that the length should be adequate to provide an increased diameter at least as long as the axial reciprocation distance of the inner sleeve within the outer tubular member.

As shown in FIG. 10, after formation as shown in FIG. 9, the enlarged diameter end 18b is polished or lapped to provide a smooth surface it its outside surface and the polished surface is then plated or coated with a harder material 18c selected for its hardness and its wear resistance, its ability to be smoothed to a working finish, and its ability to maintain a cutting edge.

FIG. 11 illustrates the final formation of the cutting end of the inner tubular sleeve 18. The enlarged end 18b with the plating or coating at 18c is again lapped or polished to provide a desired smooth and cylindrical outer surface. The leading edge of the tubular sleeve is then formed with the cutting tip at 28 and a spiral slot 30 is then cut axially along and through the enlarged portion 19b and plated portion 18c of the tube. The slot 30 preferrably extends beyond the length of the enlarged diameter portion and into the tubular stock portion 18a of the inner tubular sleeve.

The preferred steps of forming the cutting tip of the inner tubular sleeve 18 are enlarging as shown in FIG. 9, lapping the exterior surface of the enlarged portion to provide a smooth surface, coating or plating as shown in FIG. 10, lapping again to smooth the coated or plated surface, cutting the slot 30 axially and spirally along the cutting end, and then forming the cutting edge at 28. The cutting end of the inner sleeve will be formed to be truly perpendicular to the axis of the sleeve.

FIG. 3 illustrates the finished inner tubular sleeve 18 within the outer tubular member 16 and shows the original diameter tubular stock 18a, the formed diameter at 18b, and the coated or plated surface at 18c.

FIG. 7 is a more accurate representation of the relative dimensions in the formation of the inner tubular sleeve. The dimensions shown in this FIG are to be read with an understanding that there are the usual tolerances for all dimensions as might be expected in the manufacture of tubular stock or the machining or plating of that stock. In this particular sleeve construction the original tubular stock had an outside diameter of 0.0250 inches. The stock was expanded axially along the sleeve for about 0.55 inches from the end. The expanded and plated portion then had an outside diameter of 0.0275 inches including the plating of approximately 0.0003 inches. The cutting face of the inner sleeve was cut at an angle of about 30 degrees to provide a sharp cutting edge 28. The spiral slot 30 was cut at an angle of about 20 degrees to the axis of the sleeve and the slot extended about 0.75 inches axially along the sleeve. The slot 30 had a circumferential width of about 0.005 inches.

The inner tubular sleeve 18 of the dimensions shown in FIG. 7 is intended for use within an outer tubular member 16 having an inside diameter of about 0.0273 inches and a wall thickness of about 0.005 inches. It should be evident that the cutting end of the inner tubular sleeve 18 must be compressed in diameter to fit within the outer tubular member 16. The slot 30 permits that compression while providing smooth and substantially continuous circumferential contact to the inner surface of member 16. The tubular stock and the plating on its cutting end are of a material that is rigid enough to maintain an outward force on the expanded end 18b of the cutting end of the inner tubular sleeve 18; the plating of the expanded portion provides this strength to the cutting end of the sleeve. The outward force is enough to maintain a continuous working relationship between the inside edge of the outer tubular member 16 and the outside edge at the expanded end 18b of the inner tubular sleeve 18. The plating 18c is a harder material that the tubing stock 18a and is selected for its ability to provide a smooth surface and a long lasting cutting edge. A hard chrome plating is a suggested material for this service.

FIG. 6 is a perspective illustration of the inner tubular sleeve 18 showing the expanded and plated portions 18b and 18c, the cutting edge 24 and the spiral slot 30.

FIGS. 2 and 4 illustrate in cross-section and plan the exterior of the outer tubular member 16 showing the entry port 24 through the member. The entry port 24 as shown is an oval shaped opening through the outer member 16. Extending from the entry port 24 is an axial slot cutout 40. The axial slot is provided to add flexibility to the working end of the outer member 16 and to provide for radial expansion of the member 16 as the inner tubular sleeve 18 is positioned within the member 16.

When assembled as a surgical instrument with the orientation as shown in FIG. 1 the outer tubular member 16 has its port 24 and the axial slot 40 at the upper surface. The inner tubular sleeve 18 is positioned with the spiral slot 30 positioned preferrably diametrically opposite to the axial slot 40. The spiral slot 30 in the inner tubular member 18 is longer in axial dimension than the axial slot 40 in the outer tubular member 16 so that the cutting end 28 of the expanded portion of the inner tubular member 18 is always in contact with the inner surface of the outer member 16 when the inner sleeve 18 is axially oscillated within the outer member 16 during the instruments use as intended.

The axial length of slot 40 should be at least slightly less than thel ength of the expanded portion 18b of the inner sleeve 18. With that dimensional relationship the very small radial space between the outside diameter of the original tubular stock 18a would not be exposed through a slotted portion of the outer tubular member 16.

An alternative form of the entry port 24 and axial slot 40 is shown in FIG. 5. In this form the axial slot 40 is a spiral axial slot 41 extending from the entry port 24 and around the member 16. The direction of the spiral is not limiting as the intent of the spiral slot 41 is to provide for further ease in maintaining good, low friction contact between the outside of the inner sleeve and the inside of the outer member.

It should be understood that both the outer tubular member 16 and the inner tubular sleeve 18 are reasonably strong in a radial compression sense. The expanded end and the spiral slot 30 in the sleeve 30 permits the sleeve to be compressed to be inserted within the member 18. The slot 40 or 41 in the member 18 permits that member to expand slightly as the sleeve moves with respect to the entry port so as to maintain good working contact while reducing the fiction contact between the elements.

The surgical instrument of the present invention is designed to reduce the internal friction between the moving parts of the instrument and the materials and construction procedures used in its construction are used with the intention that the instrument will retain its effectiveness through multiple uses. The elements of the instrument are designed to be adapted for sterilization between uses so that a sterile instrument is available with each use. The formation of the cutting end of the inner tubular sleeve is intended to provide a cutting edge that will retain its sharpness through multiple uses. The contact between the outer surface in the inner sleeve and the inner surface of the outer member is designed to reduce the friction and thus the wear of those parts of the instrument. The clearance between the body portion of the inner tubular sleeve beyond the cutting end and toward the body of the instrument is intended to substantially eliminate contact between the sleeve and the inside of the outer member, thus reducing friction and increasing the efficiency of the cutting action of the cutting edge 28 at the entry port 24. The spiral axial slot in the inner tubular sleeve permits the inner sleeve to be readily inserted into the outer tubular member and the spiral axial slot provides for a smooth and efficient contact between the sleeve and the tubular member at the cutting end. The formation of the slot in the outer tubular member between the entry port 24 and the body portion of the instrument, whether in the straight axial form 40 or the spiral axial form 41, provides efficient contact between the sleeve and the member and reduces the friction between these two elements.

While certain preferred embodiments of the invention have been specifically disclosed, it should be understood that the invention is not limited thereto as many variations will be readily apparent to those skilled in the art and the invention is to be given its broadest possible interpertation within the terms of the following claims.

I claim:

1. In a surgical instrument including an outer tubular member having an open end and a closed end, a cutout portion through said outer tubular member defining an entry port into the interior of said outer tubular member, said entry port being located adjacent to said closed end of said outer tubular member and axially along said outer tubular member, an inner tubular sleeve having an open end and a cutting end within said outer tubular member, said cutting end of said inner tubular sleeve being formed as a circumferential edge around said inner tubular sleeve and perpendicular to the axis of said tubular sleeve, said inner tubular sleeve being adapted to reciprocate axially within said outer tubular member with said open end adjacent to said open end of said outer tubular member and said cutting end adjacent to said closed end of said outer tubular member, and a cutout portion in said inner tubular sleeve defining an axial slot beginning at said cutting end and extending toward said open end of said inner tubular sleeve, the improvement comprising:

said axial slot being cut in a spiral path axially along said inner sleeve from said cutting end and extending toward said open end thereof, and said inner tubular sleeve having an increased diameter axially along said sleeve at least as long as said axial distance of said spiral axial slot.

2. The surgical instrument of claim 1 wherein said inner tubular sleeve has an exterior coating applied to its outer surface adjacent to said cutting end thereof,
said exterior coating being applied along said inner sleeve for an axial dimension longer than said axial dimension of said entry port through said outer tubular member and at least as long as said axial distance of said spiral axial slot along said inner sleeve.

3. The surgical instrument of claim 2 wherein said inner sleeve member has an increased outside diameter at least along that portion of said sleeve where said exterior coating is applied.

4. The surgical instrument of claim 2 wherein said exterior coating is a coating of about .0003 inches thickness.

5. The surgical instrument of claim 4 wherein said coating is lapped along its exterior surface.

6. The surgical instrument of claim 1 wherein said outer tubular member is a metallic, bendable material and said inner sleeve is a metallic, bendable material, said exterior coating at said cutting end along said spiral axial slot being a hard metallic material capable of being lapped and sharpened at said cutting end.

7. The surgical instrument of claim 1 wherein said cutout portion defining said entry port is a generally enlarged opening near said closed end of said tubular member with a narrow axial slot, said narrow axial slot beginning at a portion of said port away from said closed end of said outer tubular member and extending from said enlarged opening away from said closed end toward said open end, said axial slot being of substantially constant circumferential width axially along said tubular member.

8. The surgical instrument of claim 7 wherein said axial slot in said tubular member is cut spirally along said tubular member.

* * * * *